United States Patent [19]

Santilli

[11] Patent Number: 5,334,151
[45] Date of Patent: Aug. 2, 1994

[54] DEVICE FOR CAPPING AND UNCAPPING A HYPODERMIC NEEDLE

[76] Inventor: Albert N. Santilli, 28326 Gates Mills Blvd., Pepper Pike, Ohio 44124

[21] Appl. No.: 25,544

[22] Filed: Mar. 3, 1993

[51] Int. Cl.⁵ ............................................. A61M 5/32
[52] U.S. Cl. ..................................... 604/192; 206/365
[58] Field of Search ............... 604/192, 263, 110, 197, 604/263; 206/365, 366

[56] References Cited

U.S. PATENT DOCUMENTS

| | | | |
|---|---|---|---|
| 4,836,373 | 6/1989 | Goldman | 604/263 |
| 4,852,844 | 8/1989 | Villaveces | 604/263 |
| 4,915,698 | 4/1990 | Levenson | 604/263 |
| 5,078,695 | 1/1992 | Farrar, Jr. et al. | 604/263 |
| 5,183,469 | 2/1993 | Capaccio | 604/192 |

FOREIGN PATENT DOCUMENTS 2198644  6/1988  United Kingdom ................ 604/192

Primary Examiner—John D. Yasko
Assistant Examiner—Anthony Gutowski
Attorney, Agent, or Firm—Benesch, Friedlander, Coplan & Aronoff

[57] ABSTRACT

A device for capping and uncapping a hypodermic needle includes a body portion having an opening therein through which the cap of a hypodermic needle may be inserted and removed. The body portion has a base that can be attached to a surface by an adhesive layer or by hook and loop fasteners. The body portion includes a conical helix having screw threads that engage the end of the cap upon rotation of the cap therein. Because the cap is mechanically secured by the helix, the needle can be removed or inserted into the cap while the cap is retained in place. The body portion is made of an inexpensive, resilient foam material.

15 Claims, 2 Drawing Sheets

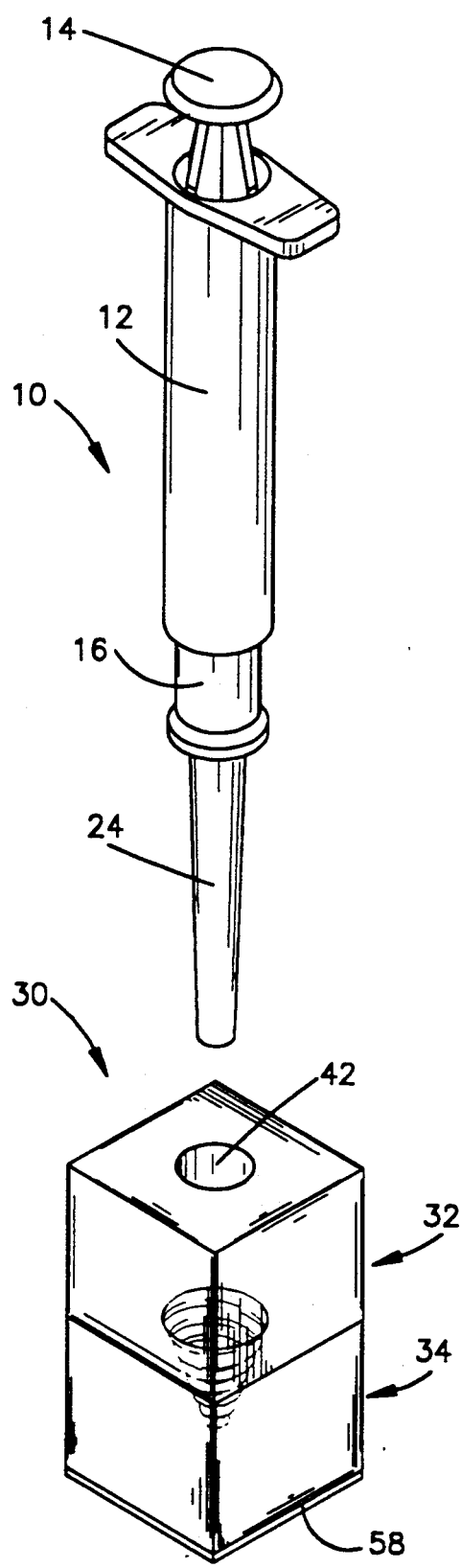
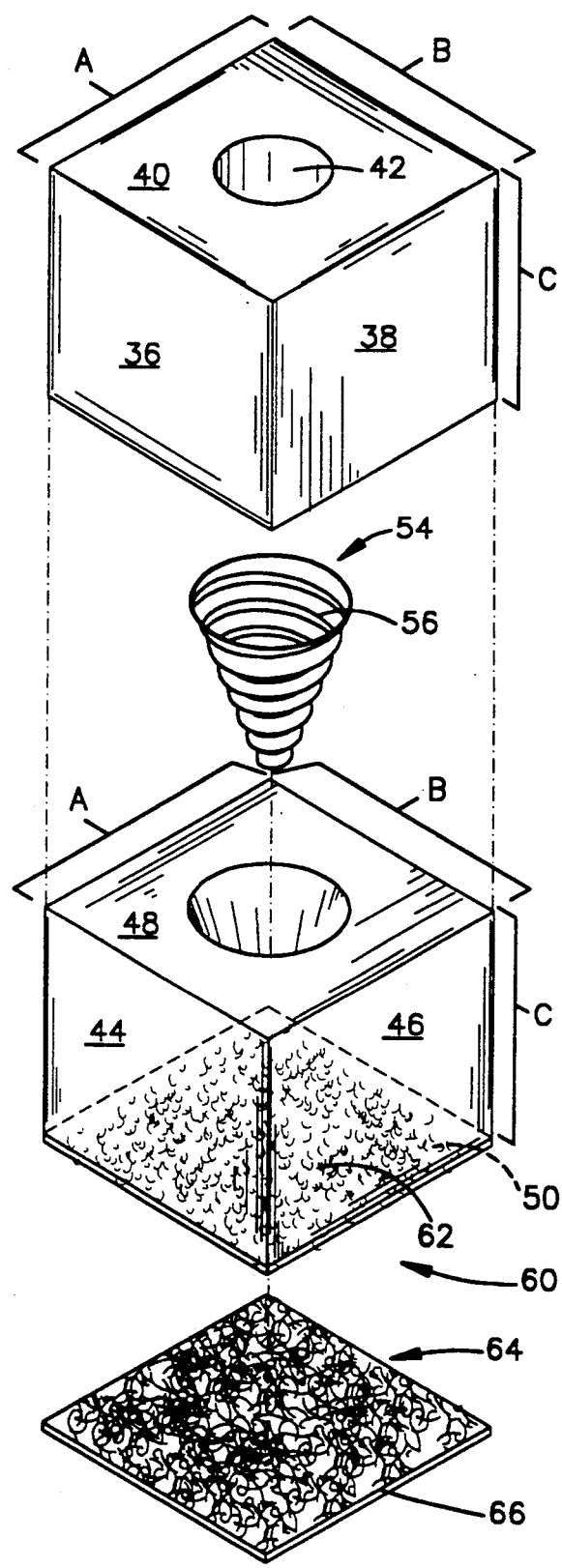
Fig.1
Fig.3

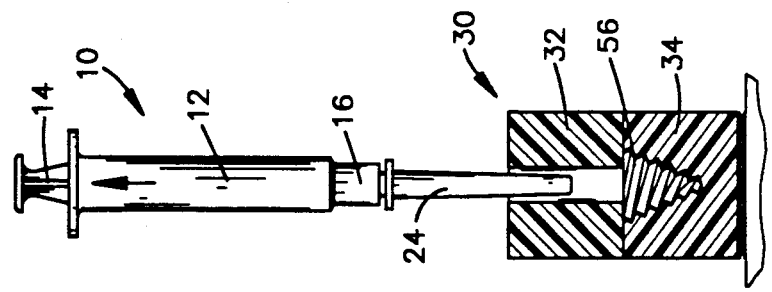
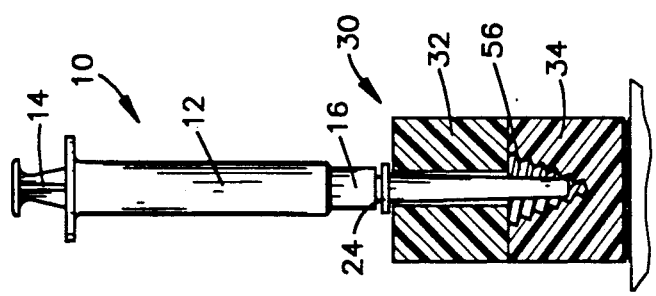
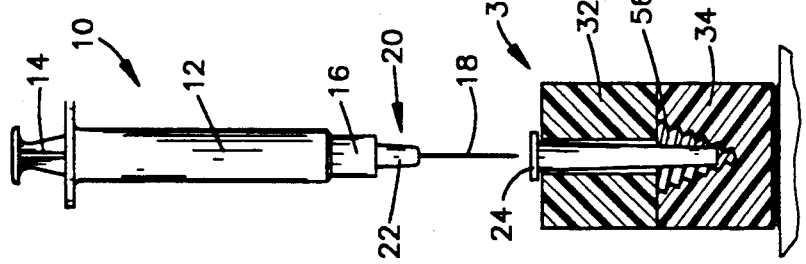
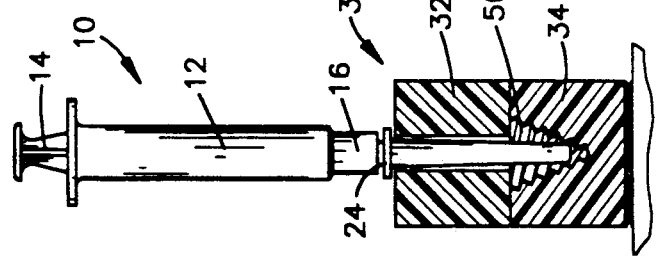
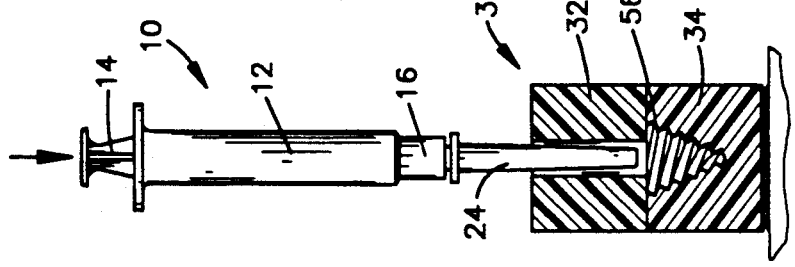

DEVICE FOR CAPPING AND UNCAPPING A HYPODERMIC NEEDLE

BACKGROUND OF THE INVENTION

1. Field of the Invention

The invention relates to hypodermic needles and, more particularly, to an inexpensive, disposable device that permits a hypodermic needle to be capped and uncapped easily.

2. Description of the Prior Art

Hypodermic needles commonly are provided with a sheath, or cap, that protects the needle while it is attached to a hypodermic syringe. The caps for hypodermic needles typically are made of a transparent or semi-transparent rigid plastic material. The caps typically are elongate, generally cylindrical members that completely cover a hypodermic needle and engage the needle-holding end of a syringe to be retained thereon.

Although hypodermic needle caps function effectively to protect hypodermic needles from contamination and damage, and to prevent unintended injury to the user, such caps can be difficult to remove. The problem is particularly acute during the course of a surgical procedure when the physician or nurse may need to have prompt access to the hypodermic syringe with its needle exposed. Frequently it is necessary or desirable to remove or replace the cap by using only one hand, but such action requires a certain amount of dexterity on the part of the user.

In an attempt to ease the difficulties associated with capping and uncapping a hypodermic needle, a device is known that holds the cap in a stable position so that the needle can be inserted into or removed from the cap. The device in question has been sold under the trademark NeedleGard II by the Plastic Engineered Products Co. of Canal Fulton, Ohio. The NeedleGard II device employs an upright body portion formed of a molded plastics material having an opening into which the cap can be inserted. The underside of the device includes a peel-away adhesive strip that enables the device to be mounted on any flat surface. Because the device can be mounted securely, and because the cap can be maintained in a stable, upright position, the needle can be capped or uncapped quickly by using only one hand.

Although the referenced device is believed to function effectively, certain problems have not been addressed. One of the most important problems relates to expense. The NeedleGard II device has a retail purchase price of approximately $14.00 (1992 dollars). It is believed that the device is sufficiently expensive that various users may not acquire the device. In other words, while the device is believed to be effective for its intended purpose, it also is believed that the device is sufficiently expensive that potential users are deterred from purchasing it.

Desirably, an inexpensive, easily usable device would be available for capping and uncapping hypodermic needles. Any such device preferably would be inexpensive enough that it could be used only once, or only during the course of a single surgical procedure, and thereafter discarded.

SUMMARY OF THE INVENTION

In response to the foregoing concerns, the present invention provides a new and improved device for capping and uncapping hypodermic needles. The device according to the invention includes a body portion having an opening therein through which the cap of a hypodermic needle my be inserted and removed. The body portion has a base that can be easily attached to a surface by means of an adhesive layer or hook and loop fasteners. The body portion includes means for mechanically gripping the cap upon insertion of the cap through the opening, said means for gripping preferably taking the form of a conical helix of a size and shape that is engageable by the cap. The screw thread portion of a conventional electrical wire nut has been found to be especially effective for this purpose.

The body portion preferably is made of an inexpensive, resilient foam material. The body portion is made in two sections that can be attached together with the conical helix secured in place within the body portion. The body portion preferably is in the shape of a small rectangular prism to facilitate compact storage and ease of manipulation.

Because the body portion and conical helix are inexpensive and easy to assemble, the entire device is sufficiently inexpensive that it can be discarded after a single use or after a single surgical procedure. Because the conical helix firmly grips needle caps of all sizes and shapes, it permits the device to be used to cap and uncap a wide variety of needles, as well as catheters and other thin, elongate objects having caps that need to be removed and applied quickly and easily during the course of a surgical or other medical procedure.

The foregoing and other features and advantages of the invention are illustrated in the drawings and are described more fully in the specification and claims that follow.

BRIEF DESCRIPTION OF THE DRAWINGS

FIG. 1 is a perspective view of a device according to the invention for capping and uncapping a hypodermic needle, and also showing a capped hypodermic syringe;

FIGS. 2A-2E are cross-sectional views of the device of FIG. 1 showing how the device is used to cap and uncap a needle attached to a hypodermic syringe; and FIG. 3 is an enlarged, exploded, perspective view of the device of FIG. 1.

DESCRIPTION OF THE PREFERRED EMBODIMENT

Referring to FIGS. 1-3, a capped hypodermic syringe is indicated generally by the reference numeral 10. The syringe 10 includes a cylindrical barrel 12, a plunger 14, and a cylindrical extension 16 that projects from the barrel 12. A needle 18 is connected to the cylindrical extension 16 by means of an adapter 20 (FIG. 2C). The adapter 20 is threaded into the end of the cylindrical extension 16. The adapter 20 includes several large, longitudinally extending splines 22. An elongate, generally cylindrical cap 24 is fitted over the needle 18. The cap 24 includes a plurality of small splines (not shown) that mate with the splines 22 in order to retain the cap 24 securely on the adapter 20 and prevent relative rotation therebetween.

A device for capping and uncapping the needle 18 is indicated generally in the drawings by the reference numeral 30. The device 30 includes a first, upper section 32 and a second, lower section 34. The first section 32 is in the form of a rectangular prism having opposed pairs of side walls 36, 38, a top wall 40, a bottom wall (not shown), and an opening 42 that extends through the first section 32 and opens through the top wall 40 and the bottom wall.

The second section 34 is of the same size and shape as the first section 32 and includes pairs of opposed side walls 44, 46, a top wall 48, and a bottom wall 50. A conical depression 52 is formed in the second section 34, which depression 52 opens through the top wall 48. A conical helix 54 is disposed within the depression 52. The helix 54 includes a plurality of screw threads 56.

The dimensions of the device 30 are indicated in FIG. 3. Dimension A is the width of the side walls 38, dimension B is the width of the side walls 36, and dimension C is the height of the side walls 36, 38. Dimensions A, B, and C also correspond to the dimensions of the corresponding side walls 44, 46 included as part of the second section 34.

In the preferred embodiment, dimension A is approximately 1.4 inches, dimension B is approximately 1.4 inches, and dimension C is approximately 1 inch. Accordingly, the device 30, in plan view, forms a square approximately 1.4 inches on each side. When viewed from the side, the device 30 is about 2 inches high. It is expected that each of the sections 32, 34 will be formed of an inexpensive, resilient foam material such as cross-linked polyethylene. Suitable material to manufacture the sections 32, 34 can be obtained from American Foam Products, Inc., Painesville, Ohio.

The conical helix 54 preferably is taken from a conventional, commercially available electrical wire nut. It is preferred that the helix 54 have a diameter of about 0.4 inch at its upper end, and that the helix 54 extend about 0.75 inch into the second section 34. Also, it is preferred that the helix 54 be made of metal and that the threads 56 be relatively sharp. Such a construction will ensure that caps 24 of virtually any size and shape will be grasped securely by the helix 54.

It also is possible that a conventional electric wire nut could be used intact. In such a circumstance, the depression 52 will have to be larger in order to accommodate the larger dimension of the wire nut. If the wire nut includes laterally extending flanges, or wings, then it will be necessary to form corresponding slots in the first and second sections 32, 34 in order to accommodate such flanges.

It is expected that the first and second sections 32, 34 will be assembled to that position shown in FIG. 1 by means of a suitable adhesive. Also, it is expected that the bottom wall 50 will be coated with a layer of adhesive that is protected by a removable layer 58. Accordingly, the device 30 can be attached to any convenient surface merely by removing the layer 58 and pressing the adhesive surface of the bottom wall 50 in contact with the object to which the device 30 is to be attached.

Referring now to FIG. 3, an alternate technique for attaching the device 30 to a desired surface is shown. A hook and loop fastener 60 includes hooks 62 that are secured to the bottom wall 50, and a sheet 64 of loops that interact with the hooks 62. The sheet 64 includes a peel-away, protective layer 66 that, when removed, exposes an adhesive surface included as part of the sheet 64. If the alternate attachment technique is employed, the peel-away layer 66 is removed and the sheet 64 is attached to any desired surface. Thereafter, the device 30 can be attached to the sheet 64 merely by engaging the hook 62 with the loops included as part of the sheet 64.

Operation

Referring now to FIGS. 2A-2E, operation of the device 30 will be described subsequent to its attachment to a desired surface.

1. A hypodermic syringe 10 having a cap 24 is oriented such that the cap 24 is aligned with the opening 42. The cap 24 is inserted into the opening 42 (FIG. 2A).

2. The barrel 12 is rotated clockwise until the screw threads 56 firmly engage the end of the cap 24 (FIG. 2B).

3. The barrel 12 is pulled away from the device 30 until the splined adapter 20 disengages from the cap 24 (FIG. 2C).

4. When it is desired to reattach the cap 24 to the adapter 20, the needle 18 is reinserted into the cap 24 until the splines of the cap and the splines 22 engage each other securely. Then, the barrel 12 is rotated counterclockwise (FIG. 2D), thereby disengaging the cap 24 from the screw threads 56.

5. The syringe 10 is withdrawn from the device 30 (FIG. 2E).

As will be apparent from the foregoing description, the device 30 is exceedingly inexpensive and easy to manufacture. The device 30 can be attached to any convenient surface. The user needs to employ only one hand to quickly and easily cap or uncap the needle 18. The conical helix 54 is sufficiently large that it will accommodate caps of all sizes and shapes, including hypodermic caps, phlebotomy caps, intravenous catheter caps, dental caps, and so forth. Due to the inexpensiveness of the device 30, it can be discarded after a single use or after a single surgical procedure has been completed.

Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. It is intended that the patent shall cover, by suitable expression in the appended claims, features of patentable novelty exist in the invention disclosed.

What is claimed is:

1. A device for applying a cap to, or removing a cap from, a hypodermic needle, comprising:
    a body portion comprised of resilient foam, the body portion being in the shape of a rectangular prism and having an opening therein through which the cap may be inserted and removed, the body portion including a base;
    means for attaching the base to a desired surface; and
    means for mechanically gripping the cap upon insertion of the cap through the opening, said means for gripping being disposed within the body portion and including a conical helix of a size and shape that is engageable by the cap.

2. The device of claim 1, wherein the base includes a layer of pressure-sensitive adhesive protected by a removable layer of non-stick material.

3. The device of claim 1, wherein the body portion is defined by first and second mating sections, the opening is formed as part of the first section, and the means for gripping is disposed within the second section.

4. The device of claim 1, wherein the helix includes screw threads.

5. The device of claim 1, wherein the means for attaching the base to a desired surface includes a layer of hook material attached to the base and a sheet of loop material protected by a removable layer of non-stick material, the sheet of loop material adapted to be attached to a desired surface.

6. The device of claim 1, wherein the means for attaching the base to a desired surface includes a layer of loop material attached to the base and a sheet of hook material protected by a removable layer of non-stick material, the sheet of hook material adapted to be attached to a desired surface.

7. A device for applying a cap to, or removing a cap from, a hypodermic needle, comprising:

a body portion of resilient foam material in the shape of a rectangular prism, the body portion including a first section having an opening through which the cap may be inserted and removed and a second section to which the first section is connected, the second section defining a base;

means for attaching the base to a desired surface, said means for attaching including a layer of pressure-sensitive adhesive protected by a removable layer of nonstick material; and means for mechanically gripping the cap upon insertion of the cap through the opening, the means for gripping being disposed within the second portion and including a conical helix defined by screw threads.

8. A device for applying a cap to, or removing a cap from, a hypodermic needle, comprising:

a body portion having an opening therein through which the cap may be inserted and removed, the body portion including a base;

means for attaching the base to a desired surface; and means for mechanically gripping the cap upon the insertion of the cap through the opening, said means for gripping being disposed within the body portion and including a conical helix of a size and shape that is engageable by the cap, the helix being included as part of a conventional electrical wire nut.

9. The device of claim 8, wherein the base includes a layer of pressure-sensitive adhesive protected by a removable layer of non-stick material.

10. The device of claim 8, wherein the body portion is comprised of resilient foam.

11. The device of claim 10, wherein the body portion is in the shape of a rectangular prism.

12. The device of claim 11, wherein the body portion is defined by first and second mating sections, the opening is formed as part of the first section, and the means for gripping is disposed within the second section.

13. The device of claim 8, wherein the helix includes screw threads.

14. The device of claim 8, wherein the means for attaching the base to a desired surface includes a layer of hook material attached to the base and a sheet of loop material protected by a removable layer of non-stick material, the sheet of loop material adapted to be attached to a desired surface.

15. The device of claim 8, wherein the means for attaching the base to a desired surface includes a layer of loop material attached to the base and a sheet of hook material protected by a removable layer of non-stick material, the sheet of hook material adapted to be attached to a desired surface.

* * * * *